(12) United States Patent
Schwager

(10) Patent No.: US 10,126,256 B2
(45) Date of Patent: Nov. 13, 2018

(54) METHOD AND ARRANGEMENT FOR IDENTIFYING CRYSTALLINE PHASES, A CORRESPONDING COMPUTER PROGRAM, AND A CORRESPONDING COMPUTER-READABLE STORAGE MEDIUM

(71) Applicant: Bruker Nano GmbH, Berlin (DE)

(72) Inventor: Thomas Schwager, Berlin (DE)

(73) Assignee: BRUKER NANO GMBH, Berlin (DE)

( * ) Notice: Subject to any disclaimer, the term of this patent is extended or adjusted under 35 U.S.C. 154(b) by 119 days.

(21) Appl. No.: 15/308,246

(22) PCT Filed: Mar. 31, 2015

(86) PCT No.: PCT/EP2015/057082
§ 371 (c)(1),
(2) Date: Nov. 1, 2016

(87) PCT Pub. No.: WO2015/165681
PCT Pub. Date: Nov. 5, 2015

(65) Prior Publication Data
US 2017/0167991 A1    Jun. 15, 2017

(30) Foreign Application Priority Data

May 2, 2014    (DE) .......................... 10 2014 208 295

(51) Int. Cl.
| | | |
|---|---|---|
| G01N 23/22 | (2018.01) | |
| G01N 23/2206 | (2018.01) | |
| G01N 23/203 | (2006.01) | |
| G01N 23/2252 | (2018.01) | |
| G01N 23/207 | (2018.01) | |

(52) U.S. Cl.
CPC ....... *G01N 23/2206* (2013.01); *G01N 23/203* (2013.01); *G01N 23/2076* (2013.01); *G01N 23/2252* (2013.01); *G01N 2223/605* (2013.01)

(58) Field of Classification Search
CPC ........... G01N 2223/605; G01N 23/203; G01N 23/2206; G01N 23/2252; G01N 23/20091
See application file for complete search history.

(56) References Cited

U.S. PATENT DOCUMENTS

| | | | | |
|---|---|---|---|---|
| 5,640,437 | A * | 6/1997 | Grueninger ...... | G01N 23/20016 378/46 |
| 6,835,931 | B2 * | 12/2004 | Wright .................. | G01N 23/203 250/307 |
| 8,903,040 | B2 * | 12/2014 | Maeyama ............ | G01N 23/207 378/45 |
| 9,188,555 | B2 * | 11/2015 | Owen ................. | G01N 23/2252 |
| 9,279,779 | B2 * | 3/2016 | Schwager ............ | G01N 23/203 |
| 2004/0011958 | A1 * | 1/2004 | Wright ................ | G01N 23/203 250/307 |
| 2006/0165218 | A1 * | 7/2006 | Uda ..................... | G01N 23/223 378/71 |
| 2010/0150307 | A1 * | 6/2010 | Grodzins ............. | G01N 23/223 378/45 |
| 2011/0220796 | A1 * | 9/2011 | Nicolopoulos .. | G01N 23/20058 250/307 |
| 2012/0288058 | A1 * | 11/2012 | Maeyama ............ | G01N 23/207 378/46 |
| 2015/0092921 | A1 * | 4/2015 | Hansford ............. | G01N 23/223 378/76 |
| 2015/0233843 | A1 * | 8/2015 | Schwager ............ | G01N 23/207 378/76 |
| 2015/0369760 | A1 * | 12/2015 | Penman ............... | G01N 23/203 250/307 |
| 2016/0356729 | A1 * | 12/2016 | Bauer ..................... | H01J 37/20 |

FOREIGN PATENT DOCUMENTS

DE    10 2012 219 998 A1    5/2014

OTHER PUBLICATIONS

Chen, C-L., and R. C. Thomson. "The combined use of EBSD and EDX analyses for the identification of complex intermetallic phases in multicomponent Al—Si piston alloys." Journal of Alloys and Compounds 490.1-2 (2010): 293-300.*
International Search Report dated May 29, 2015 dated Jun. 9, 2015.
English Translation of International Search Report dated May 29, 2015 dated Jun. 9, 2015.
German Search Report dated Aug. 18, 2014.
Kim et al., "Investigation into the High Temperature Oxidation of Cu-Bearing Austenitic Stainless Steel Using Simultaneous Electron Backscatter Diffraction-Energy Dispersive Spectroscopy Analysis", Corrosion Science, vol. 77, pp. 397-402, Aug. 28, 2013.
Kumar et al., "Microstructual Analysis of Lead-Free Solder Alloys", Metallurgical and Materials Transactions A, Springer-Verlag, NY, vol. 37, No. 8 pp. 2505-2514, Aug. 1, 2006.
Valerie Randle, "Applications of Electron Backscatter Diffraction to Materials Science: Status in 2009", J. Mater Sci. vol. 44, pp. 4211-4218, 2009.

* cited by examiner

*Primary Examiner* — Wyatt Stoffa
(74) *Attorney, Agent, or Firm* — Norris McLaughlin P.A.

(57) ABSTRACT

Methods and arrangements identify crystalline phases in a polycrystalline sample by determining a normalized vector p(i) for the chemical composition of the expected crystal structure, at each measurement point of the sample, recording a spectrum by means of energy-dispersive X-ray spectroscopy and determining the chemical composition, and recording an electron diffraction image and determining of the diffraction bands. The methods and arrangements also determine a normalized vector v for the chemical composition, compare the normalized vector v with each of the normalized vectors p(i) of the expected crystal structures and outputting an evaluation factor s(i) for the similarity of the vectors in each case, compare the diffraction bands with those of the expected crystal structures and outputting an evaluation factor n(i), and determining an overall quality from the two evaluation factors and identifying the crystal structure with the highest overall quality as belonging to the measurement point.

6 Claims, No Drawings

METHOD AND ARRANGEMENT FOR IDENTIFYING CRYSTALLINE PHASES, A CORRESPONDING COMPUTER PROGRAM, AND A CORRESPONDING COMPUTER-READABLE STORAGE MEDIUM

This application is the U.S. National Stage of International Application No. PCT/EP2015/057082, filed Mar. 31, 2015, which claims foreign priority benefit under 35 U.S.C. § 119 of German application 10 2014 208 295.1 filed May 2, 2014.

The invention relates to a method and an arrangement for identifying crystalline phases in a monocrystalline or polycrystalline sample, a corresponding computer program, and a corresponding computer-readable storage medium.

TECHNOLOGICAL BACKGROUND

The identification of crystallographic microstructures is of considerable importance in many fields of technology, for example in the case of metallic workpieces which are subjected to high stress, such as in aeroplanes and automobiles.

As a rule, the first thing is to find out about the chemical composition of the sample to be analyzed. A standard method of material analysis, which is used for these purposes, is energy-dispersive X-ray spectroscopy (EDX). An electron beam with uniform energy is directed to the relevant measurement point of the sample and the resulting X-ray emission is detected. The detected characteristic X-ray radiation reveals the elementary composition of the sample.

Electron Backscatter Diffraction (EBSD) is a method of structural analysis which serves to identify crystals in a sample. In this method, the diffraction of electrons on the crystal lattice (the so-called diffraction image) is evaluated for the purposes of phase analysis or crystal structure analysis. A diffraction image consists of a series of diffraction bands, the position of which depends on the crystal structure at the specific location within the sample and from the local orientation of the crystal. The evaluation of the diffraction images therefore necessarily requires knowledge of the prevailing crystal structure. The knowledge about this crystal structure is used to predict how the diffraction bands should be positioned in the diffraction image for a given orientation.

The structure data of many thousand known crystal structures, which are required to predict the diffraction bands, are compiled in databases and serve as references for identifying previously unknown phases of a measured sample. Based on said structure data, mathematical methods can be used to predict the position of the bands of interest within the patterns of a plurality of orientations. In practice, certain selection criteria, mostly relating to the chemical composition, are applied to pre-select crystal structures in the database which are expected to be present in the sample.

After the diffraction image of the sample has been obtained, the orientation is determined where the prediction is most similar to the measurement, based on the diffraction image of the unknown sample and by means of suitable search methods. If the selected crystal structure is correct, a good similarity is obtained; otherwise the similarity is poor. Examples of methods for identifying the orientation are, for example, described in the publications: Wright, S. I. and B. L. Adams: Automated Lattice Orientation Determination from Electron Backscatter Kikuchi Diffraction Patterns, Textures and Microstructures, vol. 14, pp. 273-278, 1991. doi: 10.1155/TSM.14-18.273; Schwarzer, Robert A.: Automated Crystal Lattice Orientation Mapping Using a Computer-controlled SEM, Micron, Volume 28, Number 3, June 1997, pp. 249-265(17); or Zaefferer S. and R. A. Schwarzer: On-line Interpretation of Spot and Kikuchi Patterns, Materials Science Forum Volumes 157-162 (1994) pp. 247-250.

The degree of similarity is primarily indicated by the number of diffraction bands which are successfully explained within a certain tolerance. This means a certain difference between the theoretical diffraction bands and those actually measured is accepted. The degree of this difference—the angular error—is a secondary indicator of similarity. If a sample is expected to contain several crystal structures, the evaluation procedure is repeated for all candidates. The candidate with the best similarity is identified as belonging to the specific location within the sample.

SUMMARY OF THE INVENTION

The method according to the invention for identifying crystalline phases in a monocrystalline or polycrystalline sample helps to overcome, or at least reduce, one or several drawbacks of the state of the art. To this end, the method comprises the following method steps:

a) for each crystal structure that is expected to be present in the sample, determining a normalized vector p(i) for the chemical composition of the crystal structure, wherein the basis of the vector represents elements and/or compounds and thus the coordinates of the vector comprise details about the concentration of the elements and/or compounds within the crystal structure;

b) at each measurement point of the sample,
  (i) recording a spectrum by means of energy-dispersive X-ray spectroscopy (EDX spectrum) and determining the chemical composition, and
  (ii) recording an electron diffraction image and determining of the diffraction bands;

c) determining a normalized vector v for the chemical composition at the measurement point, the coordinates of which comprise details about the concentration of the elements and/or compounds at the measurement point;

d) comparing the normalized vector v for the chemical composition at the measurement point with each of the normalized vectors p(i) of the expected crystal structures and outputting an evaluation factor s(i) for the similarity of the vectors in each case;

e) comparing the diffraction bands determined at the measurement point with the diffraction bands of the expected crystal structures and outputting an evaluation factor n(i) for the similarity of the diffraction bands; and f) determining an overall quality from the two evaluation factors s(i) and n(i) and identifying the crystal structure with the highest overall quality as belonging to the measurement point.

The invention is based on the finding that the identification of unknown crystalline phases in a polycrystalline sample can be made much faster if the chemical information is obtained by using and determining normalized vectors rather than by correlating entire data sets. To this end, the first thing is to make a list of structural information or crystal structures that are expected to be present in the sample. Said structural information includes, for example, the dimensions and shape of unit cells and/or the atomic position(s). The corresponding data sets which belong to each of these expected crystal structures contain both structural information and details about the chemical composition. The relevant diffraction bands are predicted in advance by using stored structural information. As an alternative or in addition, information on the relevant diffraction bands obtained from measured electron diffraction images can be input.

This list is an important part of the analytical question asked by the user ("where on the sample is structure A, where is structure B, etc."). The list can be produced in different ways. In a preferred embodiment of the invention, the list can be stored and later, when required, can be loaded by a program, for example an evaluation program. According to another preferred embodiment, the program remembers the lists used. Thus it is possible, for example, to employ a list used once for any number of measurements without having to compile a new list separately each time. This is of particularly advantage for (measuring) systems where routine measurements are set up.

Furthermore it is advantageous that a user has the opportunity to input the required structural information, i.e. the dimensions and shape of the unit cell and the atomic positions, into the program directly.

In addition, a preferred embodiment provides for a user to obtain or load the required information on a crystal structure from files in a universal exchange format. The most common exchange format is CIF (Crystallographic Information File); however, a series of other formats are available from individual providers. These structure files are compiled in free and commercial databases. Important providers include the AMCSD (American Mineralogist Crystal Structure Database) and the ICSD (Inorganic Crystal Structure Database). These databases have an interface (e.g. a web interface or a proprietary search program) which enables the user to search by different criteria, e.g. the presence of particular elements, type of symmetry, or similar. The search hits can be saved as CIF and loaded into an (evaluation) program according to the invention.

To prevent users from having to use external programs to make a structure search, a preferred embodiment includes the option to make the standard searches (presence of certain elements and structure names) within the (evaluation) program according to the invention (possibly on the condition that they have bought the commercial databases that may be required).

Then, in step a) of the method according to the invention, a normalized vector $p(i)$ for the chemical composition is determined. The basis of the vector represents chemical elements and/or chemical compounds and the coordinates of the vector comprise at least details about the concentration of the chemical elements and/or the chemical compounds within the crystal structure. The coordinates of the normalized vector $p(i)$ are preferably proportional to the concentration of the chemical elements and/or the chemical compounds or to the individual element abundances. The proportionality factor is to be selected such that the sum of the squares of the coordinates is one.

A preferred embodiment of the invention provides for the chemical evaluation to use fixed lists of elements and/or compounds. The order and type of the elements and/or compounds can be freely selected by a user, for example according to the elements and/or compounds expected to be present in the sample, e.g. O, Si, Fe, Cu. Thus the list is the basis of the vectors. The concentrations are entered into the components of the vector that are associated with the relevant elements and/or compounds. The vector is then normalized. To this end, all coordinates of the vector are multiplied by a common factor, which is selected such that the sum of the squares of the normalized coordinates is one. Said factor is equal to the reciprocal of the square root of the sum of the squares of the non-normalized coordinates.

In step b) of the method according to the invention, the sample is measured, recording an EDX spectrum and an electron diffraction image at each measurement point. The EDX spectrum is used to determine the elementary composition of the sample at the measurement point.

Based on the chemical composition of the sample at the measurement points obtained in step b), the concentration of the elements and/or compounds is determined.

In step c), the concentrations are simply entered into the coordinates of the vector v in the order of the element list. In the present example:

1st coordinate=concentration of oxygen,
2nd coordinate=concentration of silicon,
etc.

The vector v is then normalized. Thus the vector v represents the chemical composition at the measurement point, the coordinates comprising details about the concentration of the elements and/or compounds at the measurement point. Preferably the coordinates are again proportional to the individual element abundances. Once more the proportionality factor is to be selected such that the sum of the squares of the coordinates is one. This is done, for example, by determining the root of the sum of the squares of the coordinates and then dividing all coordinates by this value.

Next, in step d), only the normalized vectors of the measurement point and of the expected crystal structures are compared and an evaluation factor $s(i)$ for the similarity of the vectors is output as a result of this comparison in each case. The evaluation factor $s(i)$ used can in particular be the reciprocal of the distance of the normalized vector v of the chemical composition at the measurement point from the relevant normalized vector $p(i)$ of the chemical composition of the expected crystal structure. It is also conceivable to use the reciprocal of the square of said distance to determine the evaluation factor. In the aforesaid cases, the evaluation factor $s(i)$ has high values if there is good similarity.

Said comparison is made, for example, by computing the scalar product (SKP) of two vectors. If the similarity is good, this value is close to one; otherwise it is smaller, down to a minimum of $-1$. According to a preferred embodiment, the scalar product is then converted to a quality value. For example, the quality value can be determined according to $1/(1-SKP*SKP)$. In another embodiment, the square root of this value can be used instead. The quality value is high if the similarity is good. In general, the comparison can be made by projecting a first vector onto a given straight, in particular onto the straight defined by the second vector, and measuring the length of the projected vector, which length represents the quality value.

In step e), the diffraction bands determined at the measurement point are compared with the diffraction bands of the expected crystal structures and an evaluation factor $n(i)$ for the similarity of the diffraction bands is output. The value of $n(i)$ is the number of measured diffraction bands which are successfully explained by the crystal structure. The two evaluation factors $s(i)$ and $n(i)$ are finally used in step f) to determine an overall quality. In a preferred embodiment, the overall quality can be determined by adding up $n(i)$ and $s(i)$. The crystal structure with the highest overall quality is identified as belonging to the measurement point.

As an alternative, the diffraction bands (step e)) can be evaluated first, followed by the evaluation of the chemical information (steps c) and d)).

In a further embodiment, the angular error w(i) can be used in addition to the evaluation factors n(i) and s(i) to determine the overall quality. The angular error w(i) is obtained by comparing the positions of the diffraction bands which have been successfully explained with the positions of the predicted diffraction bands. It has small values if there is good similarity.

In an exemplary embodiment, the overall quality can be determined by summing up n(i) and s(i) and then subtracting w(i).

The diffraction bands represent lattice planes, which planes are represented by indicating the direction of their plane normal. This means that the plane normal representing a diffraction band can be determined for each measured diffraction band; in an exemplary embodiment, this is done by constructing the plane which passes through the centre of the measured diffraction band on the camera screen and through the measured point on the sample. In an exemplary embodiment, the angular error can be determined by determining the sum of the angles between the surface normals that represent the measured bands and the surface normals that represent the corresponding predicted bands. In a further embodiment, the mean value of the angles is determined instead of the sum of the angles. In a further embodiment, the square root of the mean value of the squares of the individual angles is used.

In a further embodiment, evaluation factors n(i), s(i) and/or w(i) that have been multiplied by weighting factors can be used to determine the overall quality instead of the values n(i), s(i) and optionally w(i), the weighting factors reflecting the relative relevance of the evaluation factors.

An arrangement according to the invention comprises at least one chip and/or processor and is configured such that a method for identifying crystalline phases in a polycrystalline sample can be carried out, said method comprising the following steps:
  a) for each crystal structure that is expected to be present in the sample, determining a normalized vector p(i) for the chemical composition of the crystal structure, wherein the basis of the vector represents elements and/or compounds and thus the coordinates of the vector comprise details about the concentration of the elements and/or compounds within the crystal structure;
  b) at each measurement point of the sample,
    (i) recording a spectrum by means of energy-dispersive X-ray spectroscopy (EDX spectrum) and determining the chemical composition, and
    (ii) recording an electron diffraction image and determining of the diffraction bands;
  c) determining a normalized vector v for the chemical composition at the measurement point, the coordinates of which comprise details about the concentration of the elements and/or compounds at the measurement point;
  d) comparing the normalized vector v for the chemical composition at the measurement point with each of the normalized vectors p(i) of the expected crystal structures and outputting an evaluation factor s(i) for the similarity of the vectors in each case;
  e) comparing the diffraction bands determined at the measurement point with the diffraction bands of the expected crystal structures and outputting an evaluation factor n(i) for the similarity of the diffraction bands; and
  f) determining an overall quality from the two evaluation factors s(i) and n(i) and identifying the crystal structure with the highest overall quality as belonging to the measurement point.

The invention further relates to a computer program which enables a data processing device to carry out a method for identifying crystalline phases in a polycrystalline sample once it has been loaded into storage means of the data processing device, said method comprising the following steps:
  a) for each crystal structure that is expected to be present in the sample, determining a normalized vector p(i) for the chemical composition of the crystal structure, wherein the basis of the vector represents elements and/or compounds and thus the coordinates of the vector comprise details about the concentration of the elements and/or compounds within the crystal structure;
  b) at each measurement point of the sample,
    (i) recording a spectrum by means of energy-dispersive X-ray spectroscopy (EDX spectrum) and determining the chemical composition, and
    (ii) recording an electron diffraction image and determining of the diffraction bands;
  c) determining a normalized vector v for the chemical composition at the measurement point, the coordinates of which comprise details about the concentration of the elements and/or compounds at the measurement point;
  d) comparing the normalized vector v for the chemical composition at the measurement point with each of the normalized vectors p(i) of the expected crystal structures and outputting an evaluation factor s(i) for the similarity of the vectors in each case;
  e) comparing the diffraction bands determined at the measurement point with the diffraction bands of the expected crystal structures and outputting an evaluation factor n(i) for the similarity of the diffraction bands; and
  f) determining an overall quality from the two evaluation factors s(i) and n(i) and identifying the crystal structure with the highest overall quality as belonging to the measurement point.

In a further preferred embodiment of the invention, the computer program according to the invention has a modular structure, wherein individual program modules are installed on different parts of the data processing device, for example a distributed system.

Advantageous embodiments include additional computer programs which can carry out further method steps or method procedures mentioned in the description.

Also, the invention relates to a computer-readable storage medium on which a program is stored which enables a data processing device to carry out a method for identifying crystalline phases in a polycrystalline sample once it has been loaded into storage means of the data processing device, said method comprising the following steps:
  a) for each crystal structure that is expected to be present in the sample, determining a normalized vector p(i) for the chemical composition of the crystal structure, wherein the basis of the vector represents elements and/or compounds and thus the coordinates of the vector comprise details about the concentration of the elements and/or compounds within the crystal structure;

The invention claimed is:

1. A method for identifying crystalline phases in a polycrystalline sample, comprising the method steps of:
   a) for each crystal structure that is expected to be present in the sample, determining a normalized vector $p(i)$ for the chemical composition of the crystal structure, wherein the basis of the vector represents elements and/or compounds and the coordinates of the vector comprise details about the concentration of the elements and/or compounds within the crystal structure;
   b) at each measurement point of the sample,
      (i) recording a spectrum by means of energy-dispersive X ray spectroscopy (EDX spectrum) and determining the chemical composition, and
      (ii) recording an electron diffraction image and determining diffraction bands;
   c) determining a normalized vector $v$ for the chemical composition at the measurement point, the coordinates of which comprise details about the concentration of the elements and/or compounds at the measurement point;
   d) comparing the normalized vector $v$ for the chemical composition at the measurement point with each of the normalized vectors $p(i)$ of the expected crystal structures and outputting an evaluation factor $s(i)$ for the similarity of the vectors in each case;
   e) comparing the diffraction bands determined at the measurement point with diffraction bands of the expected crystal structures and outputting an evaluation factor $n(i)$ for the similarity of the diffraction bands; and
   f) determining an overall quality from the two evaluation factors $s(i)$ and $n(i)$ and identifying the crystal structure with the highest overall quality as belonging to the measurement point.

2. The method according to claim 1, wherein the evaluation factor $s(i)$ from step e) is determined as the reciprocal of the distance or square of the distance of the normalized vector $v$ of the chemical composition at the measurement point from the relevant normalized vector $p(i)$ of the chemical composition of the expected crystal structures.

3. The method according to claim 1, wherein the normalization in step b) is done such that the sum of the squares of all element abundances is one.

4. The method according to claim 1, wherein an indicator of the similarity of the vectors, in particular a scalar product, is evaluated for the comparison in steps d) and/or e).

5. The method according to claim 1, wherein a list of crystal structures that are expected to be present in the sample is provided.

6. The method according to claim 5, wherein at least one of the following information is stored for each crystal structure:
   the chemical composition,
   an electron diffraction image including a plurality of diffraction bands, or
   structure data required to predict the diffraction bands.

* * * * *